United States Patent [19]

Thornfeldt

[11] Patent Number: 4,713,394

[45] Date of Patent: Dec. 15, 1987

[54] TREATMENT OF NONACNE INFLAMMATORY AND INFECTIOUS DERMATOSES AND HAIR LOSS

[76] Inventor: Carl R. Thornfeldt, 1054 NW. 2nd Ave., Ontario, Oreg. 97914

[21] Appl. No.: 873,859

[22] Filed: Jun. 11, 1986

Related U.S. Application Data

[63] Continuation-in-part of Ser. No. 820,472, Jan. 17, 1986, abandoned.

[51] Int. Cl.$^4$ .............................................. A61K 31/19
[52] U.S. Cl. ..................................... 514/574; 514/887
[58] Field of Search ......................................... 514/574

[56] References Cited

U.S. PATENT DOCUMENTS

| | | | |
|---|---|---|---|
| 4,292,326 | 2/1981 | Nazarro-Porro | 424/317 |
| 4,299,826 | 11/1981 | Luedders | 424/181 |
| 4,369,174 | 1/1983 | Nagai et al. | 424/62 |
| 4,386,104 | 5/1983 | Nazarro-Porro | 424/317 |
| 4,512,977 | 4/1985 | Lundy | 424/132 |
| 4,525,347 | 6/1985 | Inagi et al. | 424/81 |

FOREIGN PATENT DOCUMENTS 3133425 3/1983 Fed. Rep. of Germany .

OTHER PUBLICATIONS

Chemical Abstracts 54:16659c (1960).
Bargoni et al.-Italian J. Biochemistry 32:385-90 (1983).
Breathnach et al.-Br. J. Dermatology, III, 115-20 (1984).
Nazarro-Porro et al.-Br. J. Dermatology, 109, 45-48 (1983).
Moschella et al.-Dermatology, vol. 2 (1985), p. 99.
Lever et al.-Histopathology of the Skin, 6th ed. (1983).

Primary Examiner—Leonard Schenkman
Attorney, Agent, or Firm—Townsend and Townsend

[57] ABSTRACT

Dermatoses involving nonacne inflammatory dermatoses, infectious cutaneous diseases, and hair loss resulting from inflammation or hormonal anomalies are treated with dicarboxylic acids containing 7 to 13 carbon atoms, or certain mercapto derivatives or salts thereof.

5 Claims, No Drawings ved in the inflammatory process, including the inflammation which causes alopecia areata. Examples are salicylic acid, resorcinol, and sulfur. Other examples will be readily apparent to those skilled in the art.

TREATMENT OF NONACNE INFLAMMATORY AND INFECTIOUS DERMATOSES AND HAIR LOSS

This is a continuation-in-part of application Ser. No. 820,472, filed Jan. 17, 1986, now abandoned.

BACKGROUND AND SUMMARY OF THE INVENTION

This invention relates to the treatment of nonacne inflammatory dermatoses, infectious cutaneous diseases, and hair loss resulting from inflammation or hormonal anomalies. In particular, this invention is directed toward conditions involving inflammation or infection of the adnexa, dermis and epidermis or hormonal involution of hair follicles including such dermatoses as rosacea, perioral dermatitis, eczema, seborrheic dermatitis, psoriasis, tinea cruris, flat warts, alopecia areata, male pattern baldness and similar conditions.

The present invention resides in the discovery that certain dicarboxylic acids are effective in the treatment of these conditions, and represents a departure from the types of skin conditions on which such acids have previously been disclosed as effective.

U.S. Pat. Nos. 4,292,326 (Nazarro-Porro, Sept. 29, 1981) and 4,386,104 (Nazarro-Porro, May 31, 1983) disclose the use of dicarboxylic acids in the treatment of acne and melanocytic hyperpigmentary dermatoses. Acne is a sebaceous gland abnormality with inflammatory papules, pustules, and cysts and noninflammatory comedos. It afflicts teenagers and young adults. Melanocytic hyperpigmentary disorders are noninflammatory conditions involving an excess of melanin formation in the skin. The producing cells may be benign, premalignant, or malignant.

Nonacne inflammatory dermatoses are quite distinct from acne in a number of ways, including the distribution and morphology of lesions, the pathologic sites microscopically, the lack of spontaneous resolution, the types of and the response to treatment, and the age groups most susceptible. Infectious cutaneous diseases include all microbial and fungal invasive organisms and infestations that may be transmitted to other skin sites on the person or to other persons. Hair loss results from a variety of diseases including inflammatory conditions like alopecia areata and hormone hypersensitivity like male pattern baldness.

Rosacea is a chronic disease of the flush area of the face characterized by a heightened vascular response. It begins as a prominent intermittent flush which becomes permanent followed by telangectasias. Later papules and pustules but no comedos develop. It occurs most commonly in women over 30 years of age. Antibiotics and corticosteroids are commonly used for treatment, but response is usually poor.

Perioral dermatitis occurs primarily in young women and is characterized by erythema, papules, papulovesicles and intermittent eczematous plaques of the chin, nasolabial folds, and upper lip. Itching and burning are often present. The usual treatment consists of antibiotics and corticosteroids.

Seborrheic dermatitis is a histopathologically eczematous dermatosis characterized by poorly demarcated scaley erythematous patches with yellowish greasy scales. "Dandruff" is a mild form of this condition localized to the scalp. This disease may involve any one, several, or all of the following sites: scalp, eyebrows, glabella, paranasal and chin folds, ears and retroauricular sulci, presternal interscapular regions, pubic regions and intergluteal folds. Corticosteroids with tar, sulfur, or antibiotics give temporary control in some cases.

Psoriasis is a common chronic proliferative epidermal disease characterized by keratinocyte epidermal transit time being increased by ninefold. The lesions are sharply demarcated thick erythematous plaques with abundant white scale. The most commonly involved sites include elbows, knees, scalp, genitalia, and gluteal fold. Nail abnormalities are very common and joint disease occurs infrequently. Therapy ranges from topical tar, anthralin, and corticosteroids to systemic methotrexate, psoralens and ultraviolet A light, and ultraviolet B light.

Eczematous dermatitis is a pathologic state of epidermal spongiosus that is the end result of a variety of diseases. These include atopic diathesis, allergic and irritant contact reactions, photo allergic and photo toxic reactions, drug eruptions, and severe asteatosis. The site of the eruption depends on the insulating disease. Current therapy consists of topical and systemic corticosteroids and topical tar.

Tinea cruris "jock itch" is a fungal or fungal/yeast infection of the groin and pubic areas. The infecting organisms may spread to other skin areas and may be transmitted to other people. Present therapy consists of topical and systemic antibiotics.

These are examples of conditions for which it has been discovered that dicarboxylic acids within the scope of the present invention are an effective treatment when applied topically. In general, the invention applies to nonacne inflammatory and infectious conditions of the skin or the skin regions such as, for example, the dermis, epidermis and adnexa, and also to alopecias resulting from inflammatory disease states or from hormonal abnormalities.

DETAILED DESCRIPTION OF THE INVENTION

The dicarboxylic acids of the present invention are those having 7 to 13 carbon atoms, inclusive. Preferred such acids are saturated aliphatic acids, particularly straight-chain species. Those having 8–10 carbon atoms are the most preferred. Examples include azelaic (1,9-nonanedioic) acid, suberic (1,8-octanedioic) acid, sebacic (1,10-decanedioic) acid, and pimelic (1,7-heptanedioic) acid. The invention also extends to mercapto derivatives of such acids, including mono- and dimercapto derivatives, as well as salts such as, for example, sodium.

The compounds are generally applied in dermatological formulations. These include any of the various known mixtures and combinations which may be applied topically and which will permit even spreading of the active ingredient over the affected area. Examples include creams, lotions, solutions, ointments and unguents.

The concentration of the dicarboxylic acid in the formulation is not critical and may vary over a wide range. The acid concentration may indeed range as high as the upper limit of dissolvability in any given formulation. In most cases, however, best results are achieved within a range of about 2% to about 40% by weight, preferably from about 15% to about 20% by weight.

The formulation may contain additional ingredients on an optional basis, including both those which are biologically active and those which are biologically inactive. Keratolytic agents are particularly useful in some cases as added active ingredients. Examples are salicylic acid, sulfur and retinoid derivatives. Optional concentrations will vary among keratolytic agents. Salicylic acid, for example, is preferably used at about 0.5% to about 5.0%, while sulfur is preferably used at about 2.0% to about 10.0%. Appropriate concentration ranges for any particular keratolytic agent will be apparent to those skilled in the art. Examples of inactive ingredients are wetting agents, surfactants, emollients, and solvents.

The term "therapeutically effective amount" is used herein to denote any amount which will cause a substantial improvement in a disease condition (such as a subsidence of a lesion, for example) when applied to the affected area repeatedly over a period of time. The amount will vary with the condition being treated, the stage of advancement of the condition, and the type and concentration of formulation applied. Appropriate amounts in any given instance will be readily apparent to those skilled in the art or capable of determination by routine experimentation.

The compositions are generally applied in topical manner to the affected area, i.e., localized application to the skin region where the inflammation or abnormality is manifest.

The following examples are offered for illustrative purposes, and are intended neither to limit nor define the invention in any manner.

EXAMPLE 1

FORMULATIONS

Formulation A:

A vessel was charged with 10 grams of azelaic acid and 10 milliliters of absolute ethyl alcohol, and heated slowly until warm. To the resulting solution was added 50 milliliters of Vehicle/N or Solvent G. These are identical nonprescription solvent mixtures consisting of 47.5% ethyl alcohol, 4% isopropyl alcohol and purified water, laureth-4, and propylene glycol. Vehicle/N is obtained from Neutrogena Dermatologicals of Los Angeles, Calif. Solvent G is obtained from Syosset Laboratories, Inc. of Syosset, N.Y.

Formulation B:

One pound of Cetaphil cream and 90 grams of azelaic acid were heated separately until each was liquified (approximately two hours). Cetaphil cream is a commercially available nonprescription mixture of water, ethyl alcohol, propylene alcohol, sodium lauryl sulfate, stearyl alcohol, methylparaben, propylparaben and butylparaben obtainable from Owen Laboratories, San Antonio, Tex. Once the cream and acid were liquified, the acid was slowly beat into the cream to form a smooth homogeneous cream.

EXAMPLE 2

APPLICATION

Four patients with perioral dermatitis and ten patients with rosacea which had proved to be refractory to standard therapies applied either Formulation A or Formulation B above to the affected areas twice daily. After four to twelve weeks of such application, all lesions of perioral dermatitis and eight of the ten with rosacea had cleared.

EXAMPLE 3

APPLICATION

Sixteen patients suffering from refractory scalp seborrheic dermatitis applied Formulation A to their scalps twice daily. Over periods of time ranging from six to forty-two days of use, fourteen of the sixteen patients showed either significant reduction or complete clearing of the condition.

EXAMPLE 4

APPLICATION

Three patients suffering from eczematous dermatitis on the face and/or extremities applied Formulation B to the lesions three times daily for 6 weeks. The lesions substantially or completely cleared.

EXAMPLE 5

APPLICATION

Fourteen patients suffering from psoriasis were treated with either Formulation A or Formulation B applied twice daily to lesions on one half of the body. The treated lesions of eight patients substantially improved after four to twelve weeks but all the itching had resolved.

EXAMPLE 6

APPLICATION

Three patients with tinea cruris all cleared completely after two weeks of Formulation A or B used twice daily.

EXAMPLE 7

APPLICATION

Individual patients suffering from male pattern baldness and alopecia areata used Formulation B for 12 weeks three times daily. Spotty terminal hair growth developed. The new growth occurred in the region of most recent hair loss. Another patient with erythrasma, a bacterial groin infection, cleared with twice daily application of Formulation A for 2 weeks. A patient with flat warts improved with four weeks application of Formulation B twice daily.

What is claimed is:

1. A method for the treatment of skin suffering from a condition selected from the group consisting of nonacne inflammatory dermatoses, infectious cutaneous disease, and inflammatory and hormone hair loss, said method comprising applying to the affected area a therapeutically effective amount of azelaic acid.

2. A method for the treatment of skin suffering from nonacne inflammation, said method comprising applying to the affected area a therapeutically effective amount of a dermatological formulation containing from about 2% to about 40% by weight of a compound selected from the group consisting of straight-chain dicarboxylic acids having 7 to 13 carbon atoms, mercapto derivatives thereof and salts thereof.

3. A method for the treatment of skin suffering from an infectious cutaneous disease condition, said method comprising applying to the affected area a therapeutically effective amount of a dermatological formulation containing from about 2% to about 40% by weight of a compound selected from the group consisting of straight-chain dicarboxylic acids having 7 to 13 carbon atoms, mercapto derivatives thereof and salts thereof.

4. A method for the treatment of skin suffering from nonacne inflammation or infection of the dermis, epidermis, or adnexa, said method comprising applying to the affected area a therapeutically effective amount of a dermatological formulation containing from about 15% to about 20% by weight of azelaic acid.

5. A method for treatment of skin suffering hair loss resulting from inflammatory or hormonal anomalies, said method comprising applying to the affected area a therapeutically effective amount of a dermatological formulation containing from about 15% to about 20% by weight of azelaic acid.

* * * * *